(12) United States Patent
Sondek et al.

(10) Patent No.: US 7,807,400 B2
(45) Date of Patent: Oct. 5, 2010

(54) METHODS FOR IDENTIFYING CHEMICAL MODULATORS OF RAS SUPERFAMILY GTPASE ACTIVITY

(75) Inventors: John Sondek, Chapel Hill, NC (US); Rafael Rojas, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 374 days.

(21) Appl. No.: 10/593,503

(22) PCT Filed: Apr. 19, 2005

(86) PCT No.: PCT/US2005/013444

§ 371 (c)(1),
(2), (4) Date: Jul. 10, 2007

(87) PCT Pub. No.: WO2005/115482

PCT Pub. Date: Dec. 8, 2005

(65) Prior Publication Data

US 2008/0027135 A1    Jan. 31, 2008

Related U.S. Application Data

(60) Provisional application No. 60/564,470, filed on Apr. 22, 2004.

(51) Int. Cl.
*C12Q 1/42* (2006.01)
*C12Q 1/34* (2006.01)

(52) U.S. Cl. ................................ 435/21; 435/18

(58) Field of Classification Search ................ None
See application file for complete search history.

(56) References Cited

U.S. PATENT DOCUMENTS

2006/0263772 A1 * 11/2006 Shoemaker et al. ............ 435/6

OTHER PUBLICATIONS

International Search Report for PCT/US05/13444, dated Feb. 14, 2007.

Stephen et al. "The nucleocapsid protein as a target for novel anti-HIV drugs" www.currentdrugdiscovery.com, pp. 33-36, 2003.

Rojas et al. "Established and Emerging Fluorescence-Based Assays for G-Protein Function: Ras-Superfamily GTPases" *Combinatorial Chemistry & High Throughput Screening* 6(4):409 (Jun. 2003).

* cited by examiner

*Primary Examiner*—James Martinell
(74) *Attorney, Agent, or Firm*—Myers Bigel Sibley & Sajovec, P.A.

(57) ABSTRACT

The present invention provides a method of identifying a compound having the ability to modulate the guanine nucleotide exchange cycle of a Ras superfamily GTPase, comprising: a) contacting the compound with a guanine nucleotide exchange factor and a GTPase and obtaining a baseline fluorescence measurement; b) contacting the guanine nucleotide exchange factor and the GTPase without the compound and obtaining a baseline fluorescence measurement; c) adding a fluorophore-conjugated GTP to the components of (a) and (b), respectively; d) obtaining fluorescence measurements of the respective components of (c) over time; e) subtracting the respective baseline fluorescence measurements of (a) and (b) from each fluorescence measurement of (d); and f) comparing the resulting fluorescence values of (e), wherein a decrease or increase in the rate of fluorescence change with the compound as compared with the rate of fluorescence change without the compound identifies a compound having the ability to modulate the guanine nucleotide exchange cycle of a Ras superfamily GTPase. Further provided are compounds of the invention and pharmaceutical compositions comprising compounds of the invention useful for the treatment of cancer and neurological disorders.

2 Claims, 5 Drawing Sheets

A

B

METHODS FOR IDENTIFYING CHEMICAL MODULATORS OF RAS SUPERFAMILY GTPASE ACTIVITY

PRIORITY CLAIM

The present application is a 35 U.S.C. § 371 national phase application of PCT International Application No. PCT/US2005/013444, having an international filing date of Apr. 19, 2005, which claims the benefit, under 35 U.S.C. § 119(e), of U.S. Provisional Application Ser. No. 60/564,470, filed Apr. 22, 2004, the entire contents of each of which are incorporated by reference herein.

FIELD OF INVENTION

The present invention relates to compounds and methods of identifying such compounds that can act as modulators of Ras superfamily GTPase activity.

BACKGROUND OF THE INVENTION

The Ras-superfamily consists of over 150 signaling molecules that are categorized into several subfamilies based upon sequence homology. The Ras, Rho, Ran, Rab, Arf, and Rem/Rad family is made up of monomeric GTP hydrolyzing proteins (GTPases or G-proteins) of about 21 KDa that interact with and activate multiple downstream effector proteins, resulting in a variety of biological phenomena (Ehrhardt et al., *Exp. Hematol.*, 2002, 30:1089-106; Vojtek et al., *J. Biol. Chem.*, 1998, 273:19925-8; Shields et al., *Trends Cell Biol.*, 2000, 10:147-54; Reuther et al., *Curr. Opin. Cell Biol.*, 2000, 12:157-65). Similar to their large heterotrimeric G-protein α-subunit counterparts, small GTPases act as binary switches that cycle between active (GTP-bound) and inactive (GDP-bound) states. The GTP/GDP cycling of Ras superfamily GTPases is highly regulated by classes of proteins specific to each subfamily. Guanine nucleotide exchange factors (GEFs) activate GTPases by allowing GDP to become displaced by GTP. GTPase activating proteins (GAPs) cause inactivation by accelerating the intrinsic GTPase activity (thus, GTP hydrolysis) of G-proteins leading to an accumulation of inactive GDP-bound protein. Small GTPases can additionally be regulated by guanine nucleotide dissociation inhibitors (GDIs) that prevent nucleotide exchange, sequester GTPases, and block associated downstream signaling.

Members of the Ras and Rho subfamilies are the most extensively studied group of small GTPases and are essential components of the mitogenic signal transduction pathway. Extracellular stimulation of receptor tyrosine kinases, G-protein coupled receptors, or integrins can result in activation of Ras and the prototypical Rho subfamily members RhoA, Rac1, and Cdc42 (Etienne-Manneville et al., *Nature*, 2002, 420:629-35; Hall, *Science*, 1998, 279:509-14). Upstream activation of receptors such as G-protein coupled receptors, integrins, or receptor tyrosine kinases lead to RhoGEF activation at the plasma membrane. Once activated, these GTPases further propagate external signals by activating a multitude of downstream effector proteins, resulting in a diversity of cellular responses.

For example, RhoGEFs engage inactive GDP-bound Rho GTPases and facilitate their activation by catalyzing the exchange of GTP for GDP. GTP-bound Rho GTPases take on an active conformation that allows for binding of effectors and further propagation of downstream signaling pathways. The assay of the invention identifies compounds that interfere with the rate-limiting step of Rho GTPase activation; the rate limiting step being guanine nucleotide exchange by RhoGEFs. This assay can be used with virtually any Ras superfamily GTPase and its cognate GEF.

Additionally, activation of Ras and Rho family GTPases is a critical step during tumor progression and acquisition of an invasive and metastatic phenotype (Frame et al., *Curr. Opin. Genet. Dev.*, 2002, 12:36-43; Evers et al., *Eur. J. Cancer*, 2000, 36:1269-74; Boettner et al., *Gene*, 2002, 286:155-74; Sahai et al., *Nat. Rev. Cancer*, 2002, 2:133-42; Oxford et al., *Cancer Lett.*, 2003, 189:117-28). These GTPases are highly oncogenic, with over 30% of all human cancers and 90% of pancreatic cancers harboring activated Ras mutations (Oxford et al., *Cancer Lett.*, 2003, 189:117-28). Additional evidence also suggests a vital role for Rho family members during transformation and the acquisition of an invasive and metastatic phenotype by regulating the actin cytoskeleton (Fritz et al., *Br. J. Cancer*, 2002, 87:635-44; Fritz et al., *Int. J. Cancer*, 1999, 81:682-7; Clark et al., *Nature*, 2000, 406:532-5; Kleer et al., *Am. J. Pathol.*, 2002, 160:579-84). Furthermore, GEFs specific to Rho GTPases (RhoGEFs), such as Dbl (diffuse B cell lymphoma), Tiam1 (T-cell invasion and metastasis factor), and LARG (leukemia associated RhoGEF), are routinely isolated during screens for transforming oncogenes and make up one of the largest classes of human proto-oncogenes, with over 60 members (Whitehead et al., *Biochim. Biophys. Acta*, 1997, 1332:F1-23; Schmidt et al., *Genes Dev.*, 2002, 16:1587-609).

Further, evidence indicates that the GTPase proteins are also ideal targets for the treatment of neurological damage stemming from spinal cord injury and stroke, as well as neurological disorders such as Alzheimer's disease and Parkinson's disease. Even in the presence of inhibitory substrates inhibition of Rho has been shown to stimulate neurite outgrowth. (Winton et al, *J. Biol. Chem.*, 2002, 277:32820-9). Moreover, inhibition of Rho using C3-toxin-like peptides facilitates the repair of damaged spinal cords in mouse models. However, these Rho antagonists are covalent modifiers and are not inhibitors of guanine nucleotide exchange.

Due to their inherent oncogenic signaling properties and role in cancer metastasis Ras and Rho-mediated signaling events are emerging targets for anti-cancer drug discovery (Downward, *Nat. Rev. Cancer*, 2003, 3:11-22). Furthermore, the complex pathways that regulate Ras superfamily GTPases are the current focus of intensive research. For many of these pursuits there is a critical need for sensitive, real-time measurements of GTPase activation and subsequent monitoring of signaling events.

SUMMARY OF THE INVENTION

The present invention provides a method of identifying a compound having the ability to modulate the guanine nucleotide exchange cycle of a Ras superfamily GTPase, comprising: a) contacting the compound with a guanine nucleotide exchange factor and a GTPase and obtaining a baseline fluorescence measurement; b) contacting the guanine nucleotide exchange factor and the GTPase without the compound and obtaining a baseline fluorescence measurement; c) adding a fluorophore-conjugated GTP to the components of (a) and (b), respectively; d) obtaining fluorescence measurements of the respective components of (c) over time; e) subtracting the respective baseline fluorescence measurements of (a) and (b) from each fluorescence measurement of (d); and f) comparing the resulting fluorescence values of (e), wherein a decrease or increase in the rate of fluorescence change with the compound as compared with the rate of fluorescence change without the compound identifies a compound having the ability to modulate the guanine nucleotide exchange cycle of Ras superfamily GTPases.

Further provided herein is a method of identifying a compound having the ability to inhibit guanine nucleotide exchange factor activity, comprising: a) contacting the compound with a first guanine nucleotide exchange factor and a GTPase and obtaining a baseline fluorescence measurement; b) contacting the first guanine nucleotide exchange factor and the GTPase without the compound and obtaining a baseline fluorescence measurement; c) adding a fluorophore-conjugated GTP to the components of (a) and (b), respectively; d) obtaining fluorescence measurements of the respective components of (c) over time; e) subtracting the respective baseline fluorescence measurements of (a) and (b) from the fluorescence measurements of (d); f) comparing the resulting fluorescence values of (e), wherein a decrease in the rate of fluorescence change with the compound as compared with the rate of fluorescence change without the compound identifies a compound potentially having the ability to inhibit guanine nucleotide exchange factor activity; g) repeating steps a-e with a second guanine nucleotide exchange factor; and h) comparing the resulting respective fluorescence values of (g), wherein no decrease in the rate of fluorescence change with the compound as compared with the rate of fluorescence change without the compound identifies a compound having the ability to inhibit guanine exchange factor activity.

In addition, the present invention provides a method of identifying a compound having the ability to inhibit GTPase activity, comprising: a) contacting the compound with a guanine nucleotide exchange factor and a first GTPase and obtaining a baseline fluorescence measurement; b) contacting the guanine nucleotide exchange factor and the first GTPase without the compound and obtaining a baseline fluorescence measurement; c) adding a fluorophore-conjugated GTP to the components of (a) and (b), respectively; d) obtaining fluorescence measurements of the respective components of (c) over time; e) subtracting the respective baseline fluorescence measurements of (a) and (b) from the fluorescence measurements of (d); f) comparing the resulting fluorescence values of (e), wherein a decrease in the rate of fluorescence change with the compound as compared with the rate of fluorescence change without the compound identifies a compound potentially having the ability to inhibit guanine nucleotide exchange factor activity; g) repeating steps a-e with a second GTPase; and h) comparing the resulting fluorescence values of (g), wherein no decrease in the rate of fluorescence change with the compound as compared with the rate of fluorescence change without the compound identifies a compound having the ability to inhibit GTPase activity.

In a further embodiment, the present invention provides a method of identifying a compound having the ability to modulate effector/GTPase activity, comprising: a) contacting the compound with a GTPase and an effector protein and obtaining a baseline fluorescence measurement; b) obtaining a baseline fluorescence measurement of the GTPase and the effector protein without the compound; c) adding a fluorophore-conjugated GTP to the components of (a) and (b), respectively; d) obtaining fluorescence measurements of the respective components of (c) over time; e) subtracting the respective baseline fluorescence measurements of (a) and (b) from the fluorescence measurements of (d); and f) comparing the resulting fluorescence values of (e), wherein a decrease or increase in the rate of fluorescence change with the compound as compared with the rate of fluorescence change without the compound identifies a compound having the ability to modulate effector/GTPase activity.

Further provided herein is a method of treating cancer in a subject, comprising administering to the subject an effective amount of a compound of this invention, for example, 3-(3-(dihydroxy(oxido)stibino)phenyl)acrylic acid, to modulate the guanine nucleotide exchange cycle of Ras superfamily GTPases; to inhibit guanine nucleotide exchange factor activity; to inhibit GTPase activity; and/or to modulate effector/GTPase activity, thereby treating cancer in the subject.

Further provided herein is a method of treating a neurological disorder in a subject, comprising administering to the subject an effective amount of a compound of this invention, for example, 3-(3-(dihydroxy(oxido)stibino)phenyl)acrylic acid, to modulate the guanine nucleotide exchange cycle of Ras superfamily GTPases; to inhibit guanine nucleotide exchange factor activity; to inhibit GTPase activity; and/or to modulate effector/GTPase activity, thereby treating the neurological disorder in the subject.

In further embodiments, the present invention provides a method of modulating the guanine nucleotide exchange cycle of a Ras superfamily GTPase; of inhibiting guanine nucleotide exchange factor activity; of inhibiting GTPase activity; and/or of modulating effector/GTPase activity in a cell, comprising contacting the cell with a compound of this invention (e.g., 3-(3-(dihydroxy(oxido)stibino)phenyl)acrylic acid).

An additional embodiment of this invention provides a composition comprising 3-(3-(dihydroxy(oxido)stibino)phenyl)acrylic acid, and a pharmaceutically acceptable carrier.

DETAILED DESCRIPTION OF THE INVENTION

Figure 1:
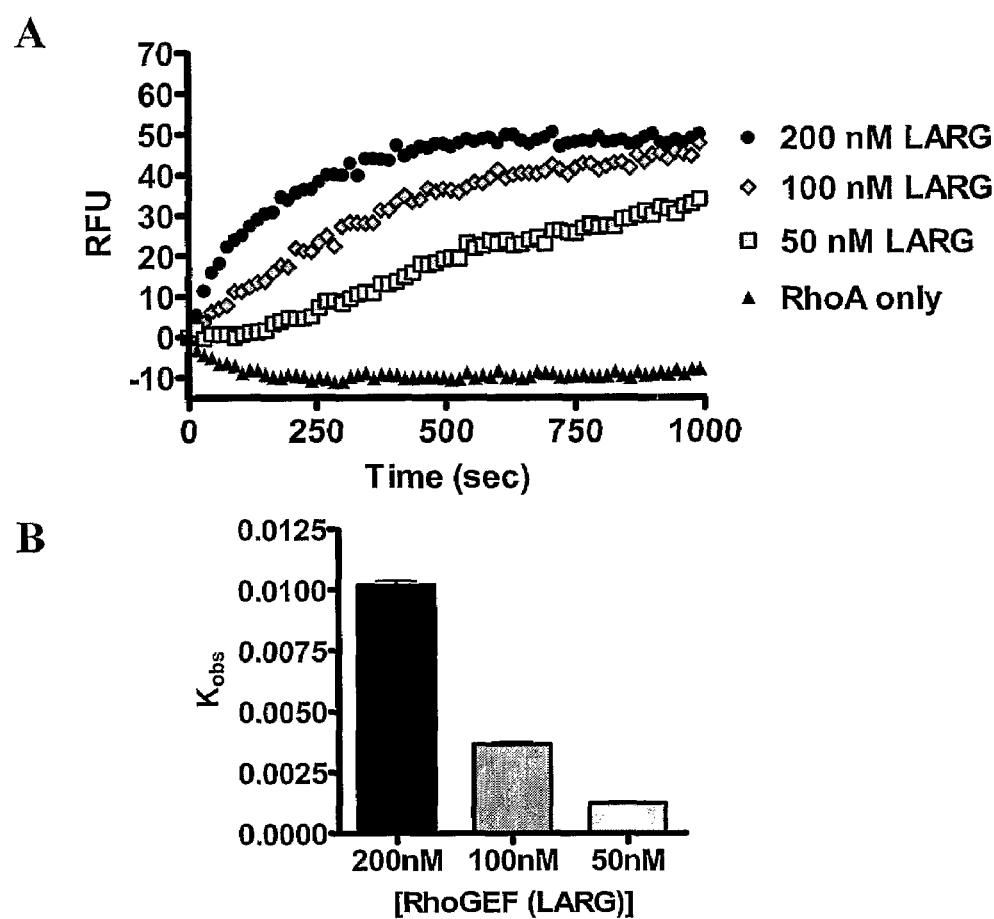
FIGS. 1A-B show the real-time fluorescence based measurement of guanine nucleotide exchange in a microtiter format. A: increasing amounts of RhoGEF (LARG) were added to GTPase (RhoA) in order to initiate nucleotide exchange in a 96-well formatted assay with a total volume of 100 µL. B: Curves were fit to an exponential growth function to determine the kinetic rates of exchange, which are plotted as a bar graph. The rate of guanine nucleotide exchange is directly proportional to the amount of RhoGEF added. Relative Fluorescence Units (RFU); observed reaction rate ($K_{obs}$)

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

The present invention is described in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

As described herein, a high throughput fluorescence based nucleotide exchange assay is provided that can be used to identify compounds that modulate (inhibit and/or activate) the guanine nucleotide exchange cycle of Ras superfamily GTPases. The invention takes advantages of spectroscopic differences between bound and unbound fluorescent nucleotide analogs to monitor guanine exchange. Fluorophore-conjugated nucleotides have a low quantum yield of fluorescence in solution due to intermolecular quenching by solvent and intramolecular quenching by the guanine base. However, upon binding to G-protein, the fluorescence emission intensity from the fluorophore is greatly enhanced. The fluorescence based nucleotide exchange assay of the present invention is highly versatile because it can be used to identify compounds that act via different mechanisms, all of which directly impact the nature of guanine nucleotide exchange. In this manner, the assay allows for identification of compounds that can act on the guanine nucleotide exchange factors (GEF) and/or the GTPases. Furthermore, the assay of the invention can be utilized to identify either inhibitors with decreased kinetics and/or activators with increased kinetics. An important use for the assays of this invention is in screening compound libraries for drug discovery. However, these assays can also be used to rapidly characterize the biochemistry of any Ras superfamily GTPase and its corresponding regulatory proteins.

As summarized above, the present invention provides methods of identifying compounds having the ability to modulate the guanine nucleotide exchange cycle of a Ras superfamily GTPase based on a high throughput fluorescence based nucleotide exchange assay. The modulation of GTPases by such compounds can occur either by direct interaction with the GTPases or indirectly by interaction with other modulators of GTPases, or by interaction with effectors downstream of the GTPase signaling pathway. Thus, in one embodiment, the present invention provides a method of identifying compounds having the ability to modulate the guanine nucleotide exchange cycle of a Ras superfamily GTPase comprising: a) contacting the compound with a guanine nucleotide exchange factor and a GTPase and obtaining a baseline fluorescence measurement; b) contacting the guanine nucleotide exchange factor and the GTPase without the compound and obtaining a baseline fluorescence measurement; c) adding a fluorophore-conjugated GTP to the components of (a) and (b), respectively; d) obtaining fluorescence measurements of the respective components of (c) over time; e) subtracting the respective baseline fluorescence measurements of (a) and (b) from each fluorescence measurement of (d); and f) comparing the resulting fluorescence values of (e), wherein a decrease or increase in the rate of fluorescence change with the compound as compared with the rate of fluorescence change without the compound identifies a compound having the ability to modulate the guanine nucleotide exchange cycle of Ras superfamily GTPases.

Additional embodiments of the invention, as described in the summary herein, provide methods for identifying compounds having the ability to inhibit GTPase activity and/or guanine nucleotide exchange factor activity according to the protocols described herein. A further embodiment of the invention provides a method for identifying compounds having the ability to modulate effector/GTPase activity according to the protocols described herein.

As used herein "a compound having the ability to modulate the guanine nucleotide exchange cycle of a Ras superfamily GTPase" is used to describe compounds capable of increasing or decreasing the rate of GTP and GDP exchange by a GTPase.

"Guanine exchange factor" as used herein describes a class of proteins that catalyze the release of GDP and thus, allow the binding of GTP. A guanine exchange factor of this invention can include, but is not limited to, Ect2, Bcr, Abr, RasGRF, Sos, Neuroblastoma, S-GEF, Vsm-RhoGEF, N-GEF, Tim, Intersectin, Xpln, Net1, LARG, p115-RhoGEF, PDZ-RhoGEF, Lfc, Lbc, p114-RhoGEF, Alsin, Tuba, P-Rex, Asef, Tiam1, Tiam2, alpha-Pix, beta-Pix, Dbs, Dbl, Trio, Duo, Duet, GEFT, Obscurin, Vav1, Vav2, Vav3, FGD1, Frabin, CDC25, ITSN, Sos1/2, any combination thereof, and/or biologically active (i.e., active in catalyzing the release of GDP) fragments or domains thereof.

"Fluorophore-conjugated" as used herein describes a fluorophore covalently attached to the sugar hydroxyl(s) of GDP, GTP or non-hydrolyzable forms of GTP. Fluorophores useful in the present invention include, but are not limited to, 4,4-difluoro-5,7-dimethyl-4-bora-3a,4a-diaza-s-indacene (BODIPY) and 2'(3')-O—(N-methylanthraniloyl-)(mant). In one embodiment of the present invention the mant fluorophore can be covalently attached to the sugar hydroxyls of GDP, GTP or non-hydrolysable forms of GTP. A further embodiment of the invention uses the BODIPY fluorophore covalently attached to the sugar hydroxyls of GDP, GTP or non-hydrolysable forms of GTP.

As used herein "non-hydrolysable forms of GTP" include, but are not limited to, GTPgamma-S and 5'-[β,γ-imido]triphosphate (Gpp(NH)p).

As used herein a "compound having the ability to inhibit GTPase activity" is used to mean a compound having the ability to block, prevent and /or reduce GTPase activity As used herein "a compound having the ability to modulate effector/GTPase activity" includes any compound having the ability to increase or decrease effector/GTPase activity.

"Effector protein" is used herein to describe a variety of proteins that are downstream signaling components, which carry out the physiological response associated with GTPase activation. Effector proteins are typically characterized by the presence of a binding domain with high sequence homology that is essential for interaction with the GTPase. Effector proteins useful in the present invention include, but are not limited to, p21-activated kinase (Pak), Rho-associated kinase (Rock), Raf kinase (Raf), Ra1GDS, phosphotidylinositol-3-kinase (PI3-K) Wiskott-Aldrich syndrome proteins (WASP), activated Cdc42-associate kinase (Ack), any combination thereof and/or biologically active fragments or domains thereof. In one embodiment of the present invention effector proteins that can be used include Pak, Rock, Raf, any combination thereof, and/or biologically active fragments or domains thereof.

The present invention further provides a method of treating cancer in a subject (e.g., a subject in need thereof), comprising administering to the subject an effective amount of a compound of this invention to modulate the guanine nucleotide exchange cycle of a Ras superfamily GTPase to inhibit guanine nucleotide exchange factor activity; to inhibit GTPase activity; and/or to modulate effector/GTPase activity. Also provided is a method of treating a neurological disorder in a subject, (e.g., a subject in need thereof), comprising administering to the subject an effective amount of a compound of this invention to modulate the guanine nucleotide exchange cycle of a Ras superfamily GTPase to inhibit guanine nucleotide exchange factor activity; to inhibit GTPase activity; and/or to modulate effector/GTPase activity. An example of a compound of the present invention that can be useful in the methods of treatment described herein includes, but is not limited to, 3-(3-(dihydroxy(oxido)stibino) phenyl)acrylic acid (NSC#13778; Stibinophenyl acrylic acid).

As used herein a "subject" to be treated by the compounds and methods of the present invention includes any animal that can be treated by modulating the guanine nucleotide exchange cycle of a Ras superfamily GTPase, by inhibiting guanine nucleotide exchange factor activity, and/or GTPase activity, and/or by modulating effector/GTPase activity. Thus, a subject of this invention can be a mammal, a reptile, an avian or an amphibian (e.g., mouse, bird, dog, cat, cow, horse, fish). In certain embodiments of this invention, the subject is a mammalian subject and in particular embodiment, the subject is a human.

Additional embodiments of the invention, as described herein, provide methods for modulating the guanine nucleotide exchange cycle of a Ras superfamily GTPase in a cell, comprising contacting the cell with a compound of this invention, for example, 3-(3-(dihydroxy(oxido)stibino)phenyl) acrylic acid.

Further embodiments of the invention provide methods for inhibiting guanine nucleotide exchange factor activity, and/or GTPase activity comprising contacting the cell with a compound of this invention, for example, 3-(3-(dihydroxy(oxido) stibino)phenyl)acrylic acid. An additional embodiment of the invention provides a method for modulating effector/GTPase activity comprising contacting the cell with a compound of this invention, for example, 3-(3-(dihydroxy(oxido)stibino) phenyl)acrylic acid.

The cell of these methods can be in vitro and/or in vivo (e.g., in a cell in a subject) and/or ex vivo. For example, in certain embodiments, the present invention provides a method of modulating the guanine nucleotide exchange cycle of a Ras superfamily GTPase in a subject, inhibiting guanine nucleotide exchange factor activity, and/or GTPase activity in a subject, and/or modulating effector/GTPase activity in a subject, comprising administering to the subject an effective amount of a compound of this invention.

A further embodiment of the present invention provides a composition comprising a compound of this invention and a pharmaceutically acceptable carrier. By "pharmaceutically acceptable carrier" is meant a carrier that is compatible with other ingredients in the pharmaceutical composition and that is not harmful or deleterious to the subject. The carrier can be a solid or a liquid, or both, and is preferably formulated with the composition of this invention as a unit-dose formulation, for example, a tablet, which may contain from about 0.01 or 0.5% to about 95% or 99% by weight of the composition. The pharmaceutical compositions are prepared by any of the well-known techniques of pharmacy including, but not limited to, admixing the components, optionally including one or more accessory ingredients. An example of a compound of the present invention includes 3-(3-(dihydroxy(oxido)stibino) phenyl)acrylic acid (NSC#13778; Stibinophenyl acrylic acid).

The compositions of this invention can be used, for example, in the production of a medicament for the use in treatment of a disease and/or disorder as described herein.

The compositions of this invention include those suitable for oral, rectal, topical, inhalation (e.g., via an aerosol) buccal (e.g., sub-lingual), vaginal, parenteral (e.g., subcutaneous, intramuscular, intradermal, intraarticular, intrapleural, intraperitoneal, intracerebral, intraarterial, or intravenous), topical (i.e., both skin and mucosal surfaces, including airway surfaces) and transdermal administration, although the most suitable route and dosage intervals in any given case will depend, as is well known in the art, on such factors as the species, age, gender and overall condition of the subject, the nature and severity of the condition being treated and/or on the nature of the particular composition (i.e., dosage, formulation, mode of administration) that is being administered.

An "effective amount" of a compound of this invention refers to a nontoxic but sufficient amount to provide a desired therapeutic effect. An appropriate "effective" amount in any individual case can be determined by one of ordinary skill in the art by reference to the pertinent texts and literature (e.g., *Remington's Pharmaceutical Sciences* (latest edition) and/or by using routine pharmacological procedures.

"Treat" or "treating" as used herein refers to any type of treatment that imparts a benefit to a subject that is diagnosed with, at risk of having, suspected to have and/or likely to have a disease or disorder that can be responsive in a positive way to a compound of this invention. A benefit can include an improvement in the condition of the subject (e.g., in one or more symptoms), delay and/or reversal in the progression of the condition, prevention or delay of the onset of the disease or disorder, etc.

The examples, which follow, are set forth to illustrate the present invention, and are not to be construed as limiting thereof.

EXAMPLES

Fluorescence-Based Assays

Strategies for identifying Ras-based drug targets for anti-cancer therapies have included structure-based approaches to designing competitive binding compounds, lipid modifications that intervene with the C-terminal lipidation process necessary for Ras localization to the plasma membrane and targeting downstream effectors directly, or indirectly by disrupting the interaction between the effector and activated GTPases. However, noticeably absent from these current strategies is the identification of inhibitors of guanine nucleotide exchange factors or direct inhibitors of small GTPases. This may be due to a general lack of well-suited, miniaturized assays to identify compounds that disrupt guanine nucleotide exchange, such as the fluorescent nucleotide exchange assay of the present invention.

The structural elucidation of a number of Ras superfamily members including Ras (Pai et al., *Nature*, 1989, 341:209-14; de Vos et al., *Science*, 1988, 239:888-93), Rac (Hirshberg et al., *Nat. Struct. Biol.*, 1997, 4:147-52), Rap (Nassar et al., *Nature*, 1995, 375:554-60), and Ran (Scheffzek et al., *Nature*, 1995, 374:378-81) has been instrumental in revealing a universal mechanism for nucleotide binding, GTP hydrolysis, and conformational alterations associated with the state of bound nucleotide (Vetter et al., *Science*, 2001, 294:1299-304). Small GTPases bind guanine nucleotides in a structurally well-defined nucleotide-binding pocket that uses a coordinated $Mg^{2+}$ ion essential for binding nucleotide. Lowering the concentration of $Mg^{2+}$ in solution, for example, by using a divalent chelators, such as EDTA, dramatically increases the rate of nucleotide release from G-proteins (Hall et al., *J. Biol. Chem.*, 1986, 261:10963-5). In this manner, addition of EDTA can serve as an artificial GEF for GTPase activation. Hydrolysis of bound GTP to yield GDP and inorganic phosphate is carried out by a slow intrinsic activity that, in Ras, results in a half-life of about 20 min. for bound GTP (Hall, A. et al., *J. Biol. Chem.*, 1986, 261, 10963-5). The universal switching mechanism of Ras superfamily GTPases stems from nucleotide-dependent conformational changes within two loop regions termed switch I and switch II (Vetter et al., *Science*, 2001, 294:1299-304). GTP-bound protein is in an active conformation that binds downstream effector proteins with high affinity, while GDP-bound protein is unable to interact effectively with downstream targets.

Most methods for studying the activation of Ras members have relied upon radioactive forms of guanine nucleotides (Porfiri et al., *Methods Enzymol.*, 1995, 256:85-90; Self et al., *Methods Enzymol.*, 1995, 256:67-76; Zheng et al., *Methods Enzymol.*, 1995, 256:77-84). Typically in these assays, free nucleotides and inorganic phosphate are separated from nucleotide-bound forms of GTPases using differential binding to filters or activated charcoal. Unfortunately, all such methods suffer from several intrinsic disadvantages arising from the need to separate bound and free nucleotides. These disadvantages include extensive manual manipulations, limited data collection rates, low intrinsic precision, the production of radioactive waste, and discontinuous monitoring of reaction kinetics. Furthermore, the physical separation of reactants introduces potential anomalies resulting from perturbations in reactant concentrations and the possible destabilization of native proteins.

Recent advances in spectroscopic instrumentation and the production of a variety of fluorescent analogs of guanine nucleotides have enabled fluorescence based assays, similar to those refined by Alfred Wittinghofer and colleagues (Lenzen et al., *Methods Enzymol.*, 1995, 255:95-109), to become preeminent for studying many biochemical properties of G-proteins. These assays take advantage of spectroscopic differences between bound and unbound fluorescent analogs of guanine to monitor the binding and hydrolysis of nucleotides as well as the interaction of GTPases with various effectors and regulators. The most common analogs possess either BODIPY (McEwen et al., *Anal. Biochem.*, 2001, 291:109-17) or mant (N-methylanthraniloyl) (Hiratsuka, *Biochim. Biophys. Acta*, 1983, 742, 496-508) fluorophores covalently attached to the sugar hydroxyls of GDP, GTP, or non-hydrolysable forms of GTP such as 5'-[β,γ-imido]triphosphate (Gpp(NH)p). Such nucleotide analogs can be used to study GTPases of the Ras superfamily (Neal et al., *Proc. Natl. Acad. Sci. U.S.A.*, 1990, 87:3562-5) as well as heterotrimeric G-proteins (Remmers et al., *J. Biol. Chem.*, 1994, 269:13771-8; Remmers, *Anal. Biochem.*, 1998, 257:89-94; Remmers et al., *J. Biol. Chem.*, 1996, 271:4791-7).

Fluorophores emit light at a longer wavelength ($\lambda_{em}$) when excited at a certain wavelength ($\lambda_{ex}$). For example, excitation of the mant fluorophore at 360 nm will result in a fluorescence emission at 440 nm. A fluorophore-conjugated nucleotide has a low quantum yield of fluorescence in solution due to intermolecular quenching by solvent and intramolecular quenching by the guanine base. However, upon binding to G-protein, the fluorescence emission intensity from the fluorophore is greatly enhanced. The X-ray crystal structure of Ras bound to a mant-derivatized, non-hydrolysable analog of GTP revealed that the conjugated mant fluorophore does not significantly affect nucleotide binding nor impair interactions with effector proteins (Scheidig et al., *J. Mol. Biol.*, 1995, 253:132-50).

Fluorescence-Based Assays of GTPase Activation

Guanine nucleotide exchange factors (GEFs) for specific Ras subfamilies activate GTPases and share a high degree of sequence homology, as well as structural similarity. For example, GEFs specific for the Ras subfamily (Sos1/2, CDC25) are characterized by the presence of a CDC25 homology domain (Boriack-Sjodin et al., J. *Nature*, 1998, 394:337-43), while GEFs specific for the Rho subfamily (Vav, Dbl, Tiam1, Dbs) contain tandem Dbl homology (DH) and pleckstrin homology (pH) domains (Whitehead et al., *Biochim. Biophys. Acta*, 1997, 1332:F1-23). GTPases and GEFs do not exhibit a one-to-one concordance in the pairings, as some GEFs will activate numerous related GTPases while other GEFs are highly specific for individual GTPases. However, the structural elucidation of several GEF-GTPase complexes has revealed a conserved mechanism of G-protein activation (Boriack-Sjodin et al., J. *Nature*, 1998, 394:337-43; Snyder et al., *Nat. Struct. Biol.*, 2002, 9:468-75; Renault et al., *Cell*, 2001, 105:245-55; Rossman et al., *EMBO J.*, 2002, 21:1315-26; Worthylake et al., *Nature*, 2000,408:682-8).

During the guanine nucleotide exchange cycle, GEFs function to stabilize the nucleotide-free state of the G-protein by binding to the inactive GDP-bound form. Once bound, the GEF catalyzes the expulsion of GDP and $Mg^{2+}$. In the cell, levels of GTP are much higher than GDP (about 10-fold) and nucleotide-free G-proteins rapidly bind GTP, leading to the restructuring of switches I and II associated with G-protein activation and the concomitant release of activating GEF. Since most G-proteins have similar affinities for the various guanine nucleotides and addition of fluorophores to the sugar hydroxyls does not typically alter these affinities (Lenzen et al., *Methods Enzymol.*, 1995, 255:95-109), GEFs generally catalyze the loading of GDP, GTP, or Gpp(NH)p, as well as their fluorophore-conjugated analogs, with similar efficiencies.

Fluorescence-Based Assays of Effector Coupling

Effector proteins for Ras superfamily GTPases preferentially interact with the GTP-bound form of the G-protein and function to further propagate signal transduction. Ras has a large number of effector proteins with the most characterized downstream targets in Ras-mediated transformation being Raf kinase, RalGDS, and phosphotidylinositol-3-kinase (PI3-K) (Vojtek et al., *J. Biol. Chem.*, 1998, 273:19925-8). Likewise, Rho GTPases have multiple downstream effector proteins (over 20) involved in actin cytoskeletal regulation, including p21-activated kinase (Pak), Wiskott-Aldrich syndrome proteins (WASP), Rho-associated kinase (ROCK), and activated Cdc42-associated kinase (Ack) (Hall, *Science*, 1998, 279:509-14).

Effector proteins for Ras superfamily members are typically characterized by the presence of a binding domain with high sequence homology that is essential for interaction with the GTPase. The binding interface between Ras or Rho and their associated effector proteins has been extensively characterized through structural studies including the crystal structures of Rap1A-Raf (Nassar et al., *Nature*, 1995, 375: 554-60), and Cdc42-Pak (Morreale et al., *Nat. Struct. Biol.*, 2000, 7:384-8). These studies and others have shown that GTP-dependent conformations within switch I and II of the GTPase determines effector specificity.

Example 1

Fluorescent Nucleotide Exchange Assay

According to the present invention a fluorescent nucleotide exchange assay is provided that can rapidly detect GTPase activity in real time using fluorescence spectroscopy techniques based on the use of fluorescent guanine nucleotides. This assay can be incorporated into a drug-screening platform that can detect chemical modulation (guanine nucleotide exchange), and thus, chemical modulators, of Ras and Rho GTPases in a high throughput manner.

In one embodiment of the fluorescent nucleotide exchange assay of this invention, purified components, including buffer, fluorescent nucleotide, GTPase, GEF, and any compound chosen to be tested, are added to a microtiter plate (96-well or 384-well) using liquid handling robotics. All but one reagent are added; typically the GTPase or the GEF is omitted in order to obtain a baseline fluorescence measurement from the plate reader before the reaction is initiated. This baseline can then be subtracted during the data analysis in order to compensate for any intrinsic fluorescence or quenching caused by compounds added. As one example, buffer, fluorescent guanine nucleotide, GEF (e.g., Tiam1), and compounds are added to a microtiter plate using a robotics liquid handler. An initial baseline reading is used to subtract background fluorescence, and then the final component, for example GTPase (Rac1), is added to initiate the reaction. Once the final reagent is added, the kinetic guanine nucleotide exchange reaction commences and real-time fluorescence intensity is measured as shown in FIG. 1A. Fitting the curve to an exponential growth function allows for determination of the observed reaction rate ($k_{obs}$), which is directly proportional to the amount of GEF added (FIG. 1B).

In one embodiment, the high throughput fluorescent nucleotide exchange assay consists of 100 μL total volume containing: 10% glycerol, 100 mM NaCl, 10 mM MgCl2, 40 mM Tris (pH 7.5), 400 nM GEF protein, 2 μM GTPase protein, 2 μM mant-GTP. Small molecules can be tested at concentrations up to 100 μM, with controls occurring in the presence of <1% DMSO. Ras and Rho GTPases are purified in the presence of GDP. Exchange factors for the GTPases Ras (Sos), RhoA (Dbs, Tim), Cdc42 (Dbs, ITSN), and Rac1 (Tiam1, Trio) are purified with constructs typically encoding for only the catalytic domains.

An automated Biomek FX liquid handler robot is used to add all reagents to 96-well microtiter fluorimeter plates and the assay is conducted in a 96-well compatible Gemini fluorimeter (Spectramax). The liquid handler is used to first add buffer components then, purified GEF protein, GTPase, and finally compounds. Ninety-six well-formatted small molecule libraries are used and 80 compounds are simultaneously tested in a single 96-well plate. Sixteen control reactions are incorporated into every 96-well plate with the controls containing vehicle only (1% DMSO vol/vol).

Once all reagents except for mant-GTP are added, an initial baseline fluorescence reading is taken before the exchange reaction is initiated. All fluorescence readings are measured using fluorescence spectroscopy software SOFTmax PRO (Molecular Devices). Each well is excited using the endpoint fluorescence at 258 nm and with emission measured at 440 nm with a bandpass filter set at 420 nm. This baseline reading is subsequently subtracted from the kinetic reading for graphing purposes. After the baseline reading is completed, mant-GTP is simultaneously added to each well using the Biomek FX liquid handler to initiate the exchange reaction. GTPase activation is then measured in real time using the kinetic fluorescence setting while exciting at 258 nm and measuring fluorescence at 440 nm. The bandpass filter is set to 420 nm and the interval setting is at 38 sec with 3 reads per well and 1 sec of mixing between fluorescent readings. Nucleotide exchange is monitored for 20-30 min and subsequently analyzed using GraphPad Prizm™ software (GraphPad Software, Inc.). All compounds with excessive (>2,000 RFU) or markedly reduced (<200 RFU) initial fluorescence are removed from further evaluation due to interfering fluorescence effects of the small molecule. Individual compounds are then analyzed for an increase or decrease in the catalytic exchange rate using the GraphPad Prizm™ analytical software (GraphPad Software, Inc.).

Example 2

Two Point Fluorescent Nucleotide Exchange Assay

Figure 2:
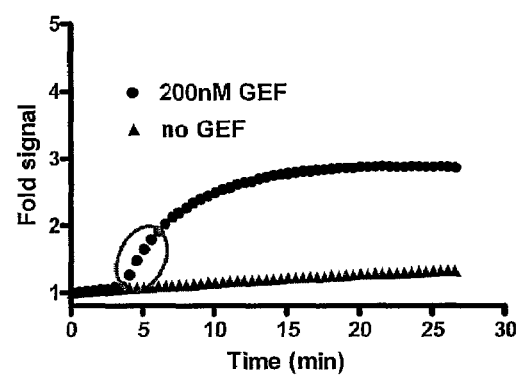
FIGS. 2A-B show the conversion of a kinetic reaction to a simplified 2-point assay. A: Typical low-throughput, fluorescence based guanine nucleotide exchange reaction occurring in a 1 mL total volume in a single cuvette. Addition of a RhoGEF (Dbs, circles) results in an increase in fluorescence over time compared to no GEF present (RhoA only, triangles). B: Adaptation to a simplified 2-point 384-well format occurring in a 50 µL total volume. Slowing the reaction kinetics and increasing the fold signal allows for reduction to a linear plot (left) that can be further reduced to only 2 points. This 2-point assay essentially extends the nearly linear initial rate of exchange, circled in the graph in A.
Figure 2:
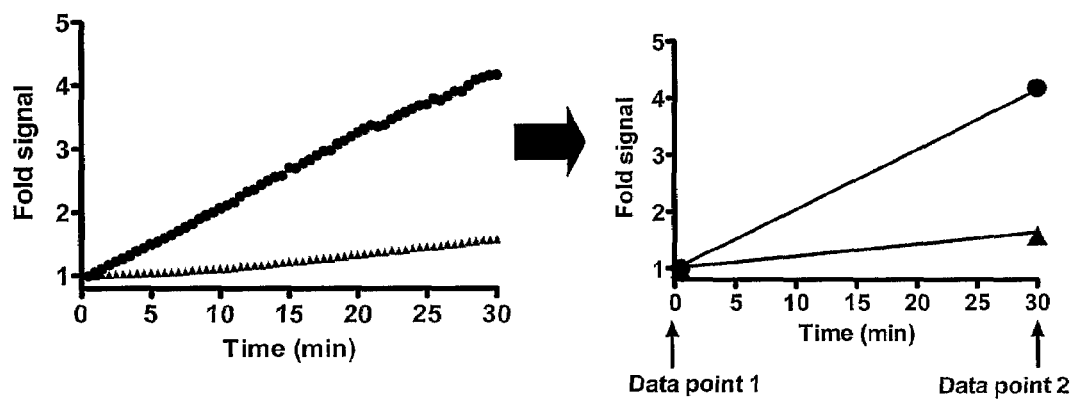

While the assay described in Example 1 is kinetic in nature and involves multiple time points in order to properly determine the rate of nucleotide exchange, the assay can also be adapted to a simple 2-point assay, thereby reducing the amount of data collection required and minimizing extensive data analysis. The conversion of a kinetic reaction as in Example 1 to a 2-point assay is shown in FIG. 2. This adaptation to a simplified 2-point assay has involved boosting signal output by using sensitive instrumentation and reducing the amount of GEF added in order to focus on the initial, nearly linear, rate of exchange.

Example 3

Refinement of the Fluorescent Nucleotide Exchange Assay

The assay of the present invention has been extensively refined in order to determine conditions that maximize signal to noise, reduce background, and translate to a simplified assay. While experimental conditions for each high-throughput screen will vary depending upon instrumentation, GEF and GTPase screened, and fluorescent nucleotide chosen, the major components used remain the same. Several different GEF-GTPase pairs have been successfully used in the 96-well real-time kinetic-based assay including the following: Tiam1-Rac1, Dbs-RhoA, Dbs-RhoB, Dbs-RhoC, Dbs-Cdc42, Trio-Rac1, Sos1-HRas, LARG-RhoA, LARG-RhoB, and LARG-RhoC, while the 2-point assay has been applied to Dbs-RhoA. The amount of GEF needed for the reaction is typically dictated by the efficiency of the GEF. For example, Tiam1 is a much less efficient GEF compared to LARG, consequently 500 nM Tiam1 and 100 nM LARG were typically used during an assay. As stated earlier, the amount of GEF present is directly related to the reaction rate.

Choice of fluorescent nucleotide will largely dictate the signal to noise ratio obtained from the assay. Both mant-GDP and BODIPY-GDP have been successfully used for compound screening, but BODIPY-GDP TR (Molecular Probes #G22351) has been found to yield a more robust signal and is less likely to interact with compounds tested. The concentration range of fluorescent nucleotide used is typically 0.25-2 µM depending on instrumentation, where a more sensitive machine can use less fluorescent nucleotide. The excitation and emission wavelengths of BODIPY can also be refined using spectrum analysis; an excitation of 590 nm and emission of 620 nm has been found to work well. The amount of GTPase present in a reaction will have the most drastic effect on signal observed and the amplitude of a reaction; therefore 1-2 µM is typically used in order to achieve a high signal.

GTPases have an intrinsic, spontaneous exchange rate that is independent of GEF activity. This spontaneous exchange is typically negligible but can contribute to background noise if the exchange rate is too high. In order to minimize spontaneous exchange rates and boost the signal to noise ratio, the buffer components can be refined dependent upon instrumentation and GTPase used. In one embodiment the buffer components include 20 mM Tris HCl (pH 7.0-7.5), 150 mM NaCl, 5-20 mM $MgCl_2$, 5-10% glycerol, 2 mM DTT, and 50 µg/mL BSA. The pH of the buffer has a small effect on reaction rates dependent on proteins used; for example, RhoA exchanges faster at pH 6.5 than at pH 7.5. This can be useful for decreasing spontaneous exchange for a screen. Additionally, $MgCl_2$, which is required for guanine nucleotide binding during the exchange reaction, can be adjusted to slow the reaction rate; for example RhoA has a slower spontaneous exchange rate at higher $MgCl_2$ concentrations.

While glycerol is typically used as a protein-stabilizing agent, which also reduces non-specific hydrophobic interactions, excessive glycerol can also negatively affect signal. Dithiothreitol (DTT) is used as a reducing agent to preserve protein integrity and also to prevent reactive compounds from causing non-specific covalent modification of proteins, which could be interpreted as false hits. The addition of BSA reduces the amount of nonspecific binding of compounds to proteins. Compounds to be screened should be added at a concentration that will result in a low hit rate (about 0.3%), which has been found to be on the order of 10-25 µM. The fluorescence exchange assay is very tolerant to DMSO, but should be limited to <5% of total volume. This assay has been successfully used in both a 96-well format and 384-well format with final volumes of 100 µL and 50 µL, respectively. When refining the assay for a particular screen, concentrations of GEF, BODIPY-GDP, GTPase, and buffer components can be adjusted depending on whether the real-time kinetic version or simplified 2-point version of the assay is being used. When employing a secondary screen to confirm activity, a different GTPase/GEF pair can be used.

Example 4

Data Analysis

Data analysis for the real-time kinetic assay is more extensive than the 2-point version, however, both utilize similar controls and have successfully been used to screen compound libraries. For each plate screened, two controls are included to assess the assay performance; DMSO is the positive control with both GEF and GTPase, while DMSO with GTPase only is the negative control. Analysis of all data involves subtracting the initial baseline fluorescence reading at time T=0 min, before the final component is added, for each individual well in order to correct for fluorescence emission or quenching caused by the compound being tested. The resulting data points in the kinetic assay are then fitted to a one phase exponential association function $[Y=Y_{max}(1-e^{(-kX)})]$, where Y is the relative fluorescence unit (RFU) response, $Y_{max}$ is the maximal response, k is the observed experimental reaction rate, and X is time. Compounds which inhibit the observed exchange rate (k) by greater than 75% compared to the DMSO only positive control are then defined as hits. The 2-point assay takes an initial reading at T=0, before the final component is added, and then takes a later time point T=30 min. "Signal" for the 2-point assay is defined as the RFU at T=30 minus the signal at T=0. This signal is then used to calculate the percent inhibition using the following formula: [Percent Inhibition=($Signal_{compound}$-$Signal_{negative\ control}$)/($Signal_{positive\ control}$-$Signal_{negative\ control}$)]. Compounds with greater that 75% inhibition are typically considered hits. Assay performance can also be assessed using standard Z-factor analyses (Zhang et al., *J. Biomol. Screen.*, 1999, 4:67-73).

Example 5

Identification of a Rac1 Specific Accelerator of Guanine Nucleotide Exchange

Figure 3:
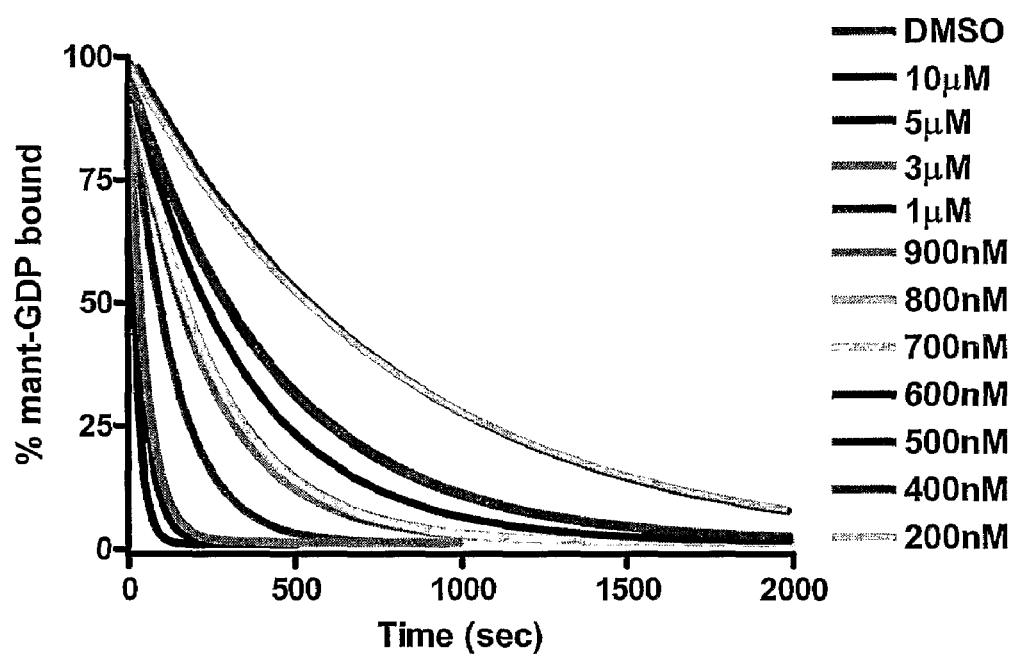
FIG. 3 shows the identification of a Rac-GEF activator using the fluorescent nucleotide exchange assay of the invention. In order to identify small molecules that modulate RhoGEF (Tiam1) activation of GTPase (Rac1) a National Cancer Institute (NCI) Diversity Set of about 2,000 compounds was screened. Most compounds tested had little affect on guanine nucleotide exchange compared to DMSO controls. However, NSC#13778 showed accelerated kinetics. Secondary studies illustrate NSC#13778 enhancing Tiam1-mediated Rac1 activation in a dose-dependent manner in a modified version of the fluorescence based guanine nucleotide exchange assay in 1 mL total volume. The structure of NSC#13778 is also shown.
Figure 3:
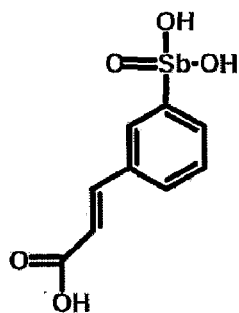

The fluorescence based guanine nucleotide exchange assay has been used to screen a publicly available National Cancer Institute (NCI) Diversity Set of about 2,000 compounds in a 96-well kinetic-based format. Additionally, about 30,000 commercially available compounds have been screened in a 384-well 2-point format. The NCI Diversity Set screen yielded a compound that acts as a Rac1 specific accelerator of guanine nucleotide exchange, although the screen was initiated to identify inhibitors of exchange. The compound is identified as 3-(3-(dihydroxy(oxido)stibino)phenyl)acrylic acid (NSC#13778, Stibinophenyl acrylic acid). This compound accelerates GEF-mediated nucleotide exchange on Rac1 in a dose-dependent manner, as shown in FIG. 3. The activity of 3-(3-(dihydroxy(oxido)stibino)phenyl)acrylic acid has been confirmed using a complementary, radiolabeled assay that shows that it is specific to Rac1, as it does not enhance nucleotide exchange on Cdc42, RhoA, or H-Ras. The compound is structurally unique with an $EC_{50}$ value in the low micromolar range (about 4 µM) and a molecular weight of 319. Structure-activity relationship studies performed on a number of related analogs have found other less active compounds, as well as compounds that are not active. The identification of 3-(3-(dihydroxy(oxido)stibino)phenyl) acrylic acid illustrates that the assay of the present invention can identify chemical modulators of GTPases.

Example 6

Biochemical Characterization of Ras-Superfamily GTPases and their Associated Guanine Nucleotide Exchange Factors (GEFs)

The 96-well formatted fluorescent nucleotide exchange assay can be utilized for a number of applications, including biochemical characterization of Ras-superfamily GTPases and their associated GEFs. Small molecule GEF inhibitors can be useful research tools to dissect signaling pathways mediated by these proteins. Additionally, compounds that target GEFs such as Tiam1 and Sos1 that are involved in disease states can be developed as a novel class of anti-cancer agents. Screening for GEF inhibitors consists of monitoring GEF-mediated nucleotide exchange on a GTPase in the presence of a chemical from a compound library as described herein. For example, this assay can be used to screen libraries for compounds that inhibit Tiam1 (GEF) mediated activation of Rac1 (GTPase). Compounds that do not affect Tiam1 will catalyze exchange similar to the controls. However, compounds that inhibit Tiam1 will not have a large increase in fluorescence. A secondary guanine nucleotide exchange reaction using an alternate GEF with the same GTPase can be used to show that the compound is GEF specific and does not alter the GTPase.

Figure 4:
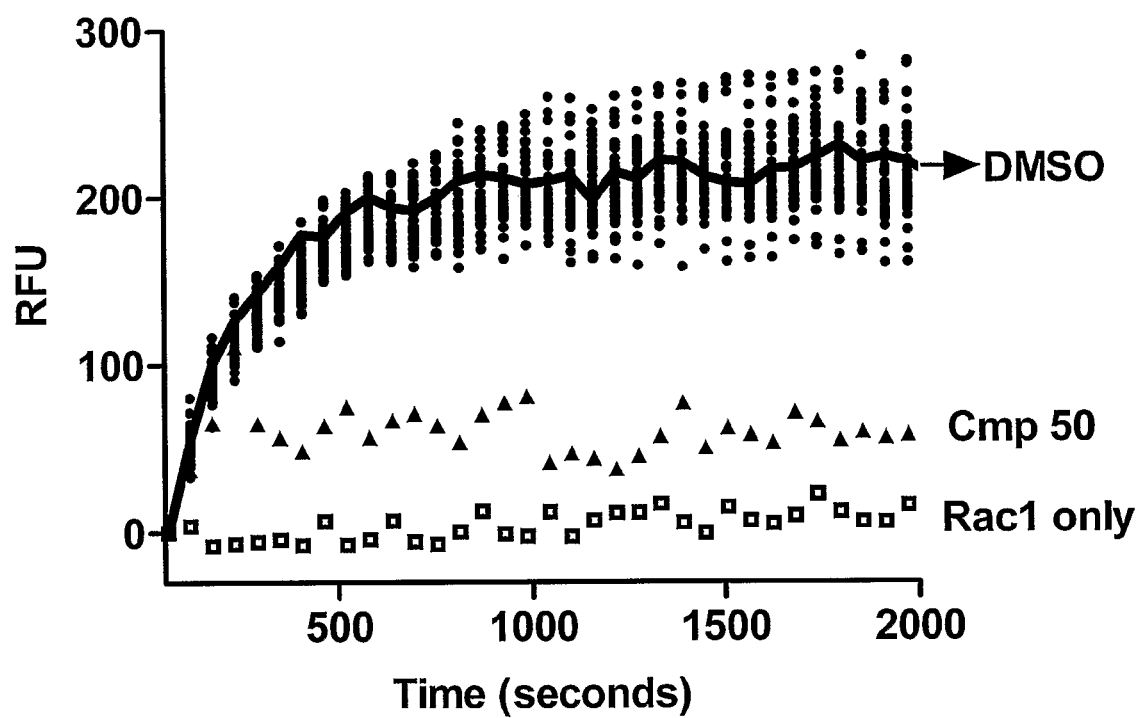
FIG. 4 shows the 96-well formatted fluorescent nucleotide exchange assay. Fifty compounds were screened for inhibition of Tiam1-mediated activation of Rac1 using a high-throughput fluorescent nucleotide exchange assay with mant-GTP. Compounds 1-49 (●) do not inhibit exchange compared to DMSO (■), while compound 50 (100 μM) (▲) inhibits Tiam1-catalyzed exchange of Rac1 similar to that of no Tiam1 present (□).

FIG. 4 shows an example wherein the assay of the invention is used to screen a large number of compounds for inhibition of Tiam1-mediated Rac1 activation. In this example, 50 compounds were screened simultaneously for their ability to disrupt Tiam1 activation of Rac1. The assay of the present invention has been shown to effectively monitor GEF-induced GTP loading onto a variety of Ras-superfamily GTPases.

Additionally, this format allows the screening of a large number of mutant protein constructs for activity and substrate specificity. Multiple truncation mutants of GEFs or point mutations of G-proteins can be readily assayed simultaneously. This approach is currently being used to analyze the substrate specificity of novel RhoGEFs against a panel of over 20 Rho GTPases.

Example 7

Identification of GTPase Inhibitors

Figure 5:
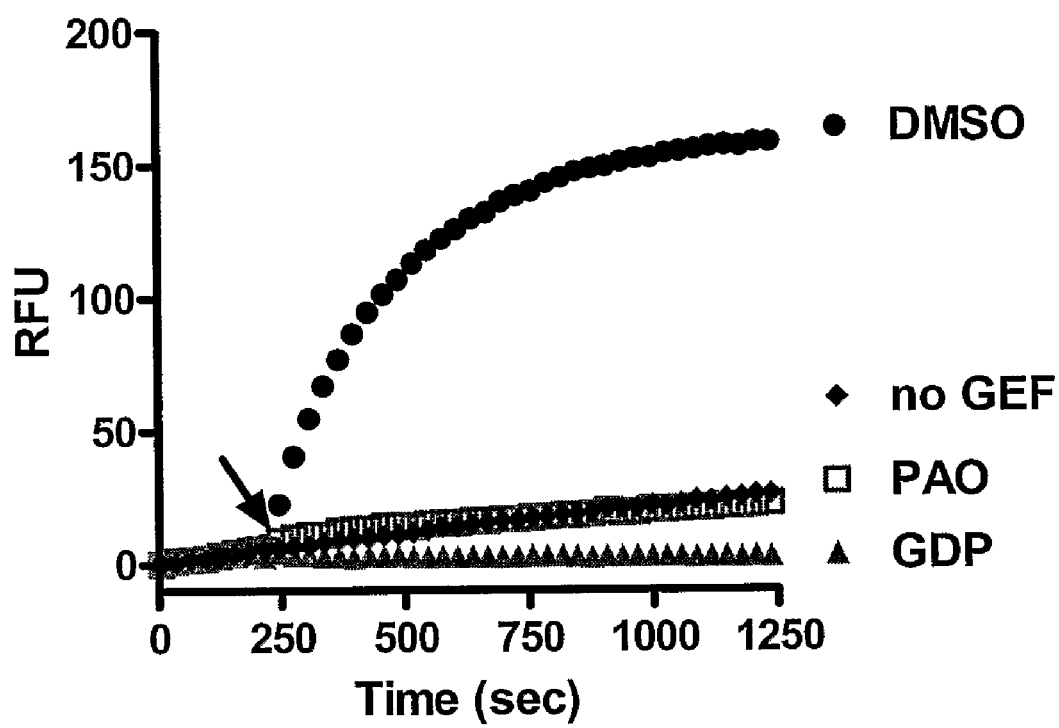
FIG. 5 shows the guanine nucleotide exchange reaction for Dbs-mediated activation of RhoA. In order to inhibit guanine nucleotide exchange, compounds may target the GTPase directly via the nucleotide-binding pocket or the conformationally flexible switch regions; alternatively, compounds may directly target the GEF (blue). The assay of the present invention is versatile because it can identify inhibitors that function via any of these mechanisms. Vehicle only control (DMSO, circles) shows robust increase in fluorescence after addition of GEF (arrow), while a covalent modifier of the RhoA switch regions (PAO, squares) inhibits RhoA activation. Additionally, a non-fluorescent guanine nucleotide (GDP, triangles), which competes for the guanine nucleotide-binding site, and absence of GEF (diamonds), both inhibit guanine nucleotide exchange. PAO=PhenylArsineOxide.

The florescence-based guanine nucleotide exchange assay is extremely versatile and could be used to identify compounds with several different mechanisms of action. Several strategies can be employed to directly target and disrupt GTPase activation by GEFs. Screening for GTPase inhibitors can be conducted essentially as outlined in Example 6. A compound that targets the GTPase directly by binding to the guanine nucleotide-binding pocket would disrupt nucleotide binding and therefore prevent exchange. This is illustrated in FIG. 5 by addition of a non-fluorescent nucleotide (GDP), which competes with mant-GDP for binding to the nucleotide-binding pocket and therefore does not demonstrate an increase in fluorescence with the addition of GEF. A compound that binds to the switch regions of the GTPase, such as PhenylArsineOxide (PAO), would prevent activation by the GEF because this is the region of the protein necessary for interacting with GEFs, as well as GAPs and effectors (Gerard et al., *Mol. Pharmacol.*, 2003, 63, 1349-55). Alternatively, targeting the GEF directly would prevent activation of the GTPase target.

While no small molecule GEF inhibitors have been described in the literature, the assay of this invention can be used to identify inhibitors of GEF function since the rate of reaction is directly proportional to the amount of GEF present as shown in FIG. 1. The data output and secondary specificity studies are useful for rapidly determining the mechanism of action of any compounds identified during a high-throughput screen.

Example 8

Identification of Effector Inhibitors

Another potential application of the guanine nucleotide exchange assay is the identification of small compound inhibitors of the effector-GTPase interaction. Effector proteins are the downstream signaling components that carry out the physiological response associated with GTPase activation. For example, a major downstream target for Rac is PAK, while Rho activates ROCK and Ras activates Raf. Small GTPases have an intrinsic rate of nucleotide exchange that, although slow, can be effectively monitored using the fluorescence based exchange assay. The binding of an effector protein to the GTPase, however, will reduce this spontaneous exchange rate dramatically. Over a period of time, a GTPase will increase fluorescence intensity in a linear fashion due to spontaneous exchange. However, the addition of an effector protein or effector binding domain will prevent spontaneous exchange by acting as a guanine dissociation inhibitor (GDI). By monitoring this increase in fluorescence in the presence of a compound library and target effector protein, this assay can be used to identify compounds that disrupt GTPase-effector interactions.

Example 9

Identification of Oncogenic Ras Inhibitors

Ras is the most frequently mutated oncogene found in human cancers and is one of the leading candidates for target-based drug design. Ras mutations render the protein resistant to RasGAP-mediated inactivation, thereby preserving the activated GTP-bound state. An emerging strategy for anti-cancer drug design is to inhibit activated Ras. One novel approach is to design compounds that allow mutated Ras to be inactivated by RasGAP. The high throughput exchange assay of the present invention can be used to screen compounds for this purpose. By monitoring distinct fluorescent signals generated by GTP-bound and GDP-bound mutated Ras, large compound libraries can be screened to identify compounds with the ability to inactivate mutated Ras.

Example 10

G-protein Coupled Receptor (GPCR) Screen

While many drugs on the market today work by modulating G-protein coupled receptor (GPCR) signaling, there are not many in vitro, fluorescence-based high throughput assays to screen for such chemical modulators of GPCR signaling. The high throughput guanine nucleotide exchange assay of the present invention can be used to screen purified GPCRs for chemical agonists. Activated GPCRs function as GEFs for G-protein alpha subunits. These G-proteins are significantly different from the Ras superfamily, however they still cycle between GTP-bound ON and GDP-bound OFF states much like Ras GTPases. By reconstituting the GPCR, G-protein alpha subunit system in lipid vesicles, activation can be monitored using the fluorescence-based guanine nucleotide exchange assay. This application has enormous potential for the rapid screening of novel high affinity ligands for many validated GPCR targets.

Example 11

Rho Family G-Proteins and Cancer

Rho family G proteins coordinately control cytoskeletal rearrangements and transcriptional events necessary for various cellular process involving alterations in cell shape including: migration, cytokinesis, axonal growth, cellular polarity and differentiation. Like the majority of G-proteins, members of the Rho family (typified by RhoA, Rac1, and Cdc42), cycle between inactive and active forms dictated by the state of bound guanine nucleotide. G proteins bound to GDP are inactive in downstream signaling while GTP-bound forms have increased affinity for a plethora of downstream effector proteins. Auxiliary proteins at several points normally tightly control cycling between GDP and GTP-forms. Dysregulation at any of these control steps can alter the regulated balance of active and inactive G proteins leading to aberrant signaling cascades and a variety of associated abnormalities. ("Rho family" document)

GEFs for Rho family members are characterized by a tandem array consisting of a Dbl homology (DH) domain invariantly associated with an adjacent, C-terminal pleckstrin homology (PH) domain. Exchange activity predominantly localizes to DH domains while associated PH domains can regulate exchange activity by a variety of mechanisms that are not completely understood. Aside from the universal requirement for associated DH and PH domains, Dbl-related GEFs vary widely in primary sequence and domain architecture, and comprise a large family of greater than 50 distinct eucaryotic members. Typically, overexpression or truncation of Dbl-related GEFs to remove auto-inhibitory sequences favors GTP loading onto various Rho family members. Consequently, many Dbl-related GEFs have been isolated based upon their tumorigenic potential in various cell-based assays. Clinically, chromosomal translocations leading to disruption of the Dbl-related GEFs bcr, abl, and LARG are associated with chronic myelogenous and acute lymphocytic leukemias while similar disruption of FGD1 leads to the developmental abnormality faciodigitogenital syndrome, also known as Aarskog-Scott Syndrome.

An understanding of the activation of Rho family G-proteins by Dbl-related GEFs is necessary in order to predict and control associated cellular processes. Toward this end, the crystal structures have been solved for several DH/PH fragments bound to their cognate Rho family G proteins depleted of guanine nucleotide (Tiam1/Rac1, Dbs/Cdc42, Intersectin/Cdc42). Since Dbl-related GEFs show a wide range of specificities and promiscuities for Rho family G-proteins, these crystal structures present a detailed framework for understanding the various couplings between Rho-family G proteins and their associated GEFs.

Thus, an embodiment of the present invention is provided that is directed to a high throughput screening (HTS) assay to screen for compounds that interfere with the activation of Rho family G proteins by Dbl-related GEFs. This assay detects the inhibition of activation of the Rho family G-proteins using the loading and unloading of fluorescent analogs of GDP and GTP onto Rho family G-proteins. Compounds identified through these screening procedures can be further characterized for efficacy in cell-based assays as exchange factor inhibitors. Ultimately, this research allows for the identification of lead compounds for inhibition of abnormally activated G-proteins and the amelioration of associated pathologies, including cancer.

Exchange assays and high throughput screening (HTS). The current fluorescence-based assays used to measure exchange activity of Dbl-related GEFs use GDP and GTP derivatized at the 2' or 3' hydroxyls with methyl-anthronyl (mant). The fluorescent quantum yields of mant-guanine nucleotides dramatically increase upon binding to G proteins, and this characteristic provides quantitative, real-time measurements of bound vs. free nucleotide. Typically, exchange reactions are performed in 2 ml cuvettes with limiting concentrations of mant-guanine nucleotides relative to G protein. Spontaneous exchange of mant-guanine nucleotides onto Rho family G proteins is relatively slow and significant loading of the fluorescent guanine nucleotides with consequent increases in fluorescence is initiated by the addition of catalytic amounts of GEF. The assay requires no washing, filtering, or removal of reagents, and yields reproducible initial rates of loading and unloading of guanine nucleotides bound to G proteins. Furthermore, Cdc42, RhoA, and Rac1 loaded with mant-nucleotides are stable for several hours under the reaction conditions, fulfilling an obvious requirement of high throughput screening when sample preparation and fluorescence measuring are time-consuming.

While these assays are adequate for the routine analysis of distinct GEFs with specific Rho family G proteins, several parameters are unacceptable for high-throughput screening. The present invention converts the cuvette format to 96-well microtiter plates using a SpectroMax Gemini spectrofluorimeter plate reader (Molecular Devices) with dual monochromators for independent excitation and emission wavelength selection. Compounds to be screened are diluted into DMSO, added to duplicate wells of a microtiter plate, and dried. Subsequently, GEFs are added and allowed to incubate with compounds before addition of G proteins. Prior to the addition of fluorescent nucleotides, the plates are scanned and wells with excessive autofluorescence are recorded as potentially confounding to subsequent analysis. Guanine nucleotide exchange is initiated with the addition of mant-GTP that is allowed to incubate before reading. If necessary to allow post-reaction manipulations, exchange is significantly quenched by the addition of millimolar concentrations of $Mg^{2+}$ that stabilizes bound guanine nucleotide and incubation at 4° C. Efficacious inhibitors of GEF-catalyzed exchange are anticipated to significantly reduce overall fluorescence.

The current techniques rely upon prompt fluorescence defined as the direct measurement of emitted fluorescence after excitation at a specific wavelength. However, while prompt fluorescence can be used for HTS, several alternate techniques can also be employed. For instance, fluorescence anisotropy (FA) measures changes in fluorescence polarization due to molecular motion. This technique is inherently ratiometric and is therefore less prone than prompt fluorescence to inner filter effects and autofluorescence from additional components introduced during screening of chemical libraries. The binding of mant-GDP to Rho family G proteins (about 20 kDa) represents a large change in the effective size of the fluorescent marker. Therefore tumbling rates and associated anisotropies of mant-GDP are expected to be significantly altered upon binding G proteins, thereby allowing sensitive monitoring of exchange events.

The use of intramolecular resonance energy transfer using guanine nucleotides derivatized with BODIPY at the 2' or 3' hydroxyls is also included within the embodiment of this invention. Unbound BODIPY-guanine nucleotides are internally quenched due to the interaction of the fluorescent group with the guanine base. Upon interaction with G proteins, the guanine nucleotide base is sequestered from solvent and inaccessible to the BODIPY derivative, resulting in a large increase in the fluorescent quantum yield of BODIPY. Since internal quenching serves to reduce background fluorescence, exchange techniques using BODIPY derivatives are anticipated to produce significant improvement in signal to noise relative to similar mant derivatives.

Specific GEF/G protein systems RhoA, Rac1, and Cdc42 are typically studied as representative members of the Rho family of G proteins responsible for distinct morphological alterations in response to unique extracellular signals. Currently, several Dbl-related GEFs with varying activity toward these Rho family members are being studied. For instance, Tiam1 possesses exchange activity only toward Rac1, while intersectin is specific for Cdc42, and Dbs will exchange on both RhoA and Cdc42. The characterization of these mammalian GEFs provides a spectrum of exchange activities to profile against any compounds identified through HTS. In some embodiments, the HTS assays of this invention will involve Tiam1 prior to complementary studies with either Dbs or intersectin.

Tiam1, or T-cell lymphoma invasion and metastasis factor 1 was originally identified by its ability to promote invasiveness of a normally non-invasive T-cell lymphoma. Similarly, Tiam1 promotes metastasis of these clonal cell lines upon injection into nude mice. Dbs was also isolated based upon its transforming potential while intersectin couples proto-oncogenic Ras to the Rho family of G proteins.

The extensive and on-going characterization of Dbl-related GEFs provides unique opportunities to develop HTS techniques for development of lead compounds designed to inhibit a central control point of G-protein activation that upon dysregulation promotes cancer.

Example 12

Standard Assays of Nucleotide Exchange

The simplest fluorescence based assay of nucleotide exchange is straightforward, rapid, and typically sufficient for monitoring GTPase activation in real-time. This assay is useful for assessing the competence of GTPases to bind guanine nucleotides in the presence of limiting concentrations of $Mg^{2+}$ as well as for the biochemical characterization of GEFs. In this assay, a candidate GEF (or EDTA) catalyzes the expulsion of nucleotide from the small GTPase. Then, depending on which fluorescent nucleotide is predominant in solution, the fluorophore-conjugated nucleotide binds to the GTPase thereby causing an increase in the fluorescent signal. Fluorophores conjugated to both GDP and GTP can be used for this assay, as they will both bind to nucleotide-free G-protein. The GTPase is typically purified in a buffer containing GDP, to facilitate interactions between the GEF and GTPase and assure a low level of spontaneous nucleotide loading.

A typical example of a fluorescent nucleotide exchange assay incorporating mant-GTP is as follows. Experimental conditions for this particular result are typical for fluorescent nucleotide exchange assays and can be applied to most studies of small GTPase activation. Rac1 was purified in the presence of GDP and the catalytic DH/PH fragment of Tiam1 was used as an exchange factor. Typical reaction conditions are: 10% glycerol (v/v), 50 µg/mL bovine serum albumin (BSA), 20 mM Tris (pH 7.5), 150 mM NaCl, 1 mM dithiothreitol (DTT), 10 mM $MgCl_2$, 400 nM mant-GTP, 200 nM GEF (Tiam1), and 2 µM GTPase (Rac1) in 1 mL total volume. For this example of Tiam1 activation of Rac1, a reaction containing all reagents except for Tiam1 was allowed to equilibrate for about 500 seconds in a 1500 µL thermostatted cuvette (25° C.) with constant stirring. After this initial equilibration, Tiam1 was manually injected into the mixture to initiate the exchange reaction. Fluorescence emission was then monitored until completion using a Perkin-Elmer LS-55 fluorimeter with the following settings: $\lambda_{ex}$=360 nm, $\lambda_{em}$=440 nm, slits=5/5 nm.

While this simple fluorescent nucleotide exchange assay is sufficient to describe relative levels of GTPase activation in a format that is readily applicable to most GTPases, it is not sensitive enough to determine catalytic rates of reaction. The major problem is that fluorescent nucleotide reactants in solution are typically in limiting quantities, i.e., only 400 nM. This dilemma can easily be circumvented by increasing the concentration of fluorescent nucleotides in solution to non-limiting quantities (about 100 µM). However, given the cost of purchasing or synthesizing large quantities of fluorescent nucleotides, this remedy is often impractical. Consequently, kinetic data is typically collected using G-proteins preloaded with fluorescent guanine nucleotides as described in Example 13.

Example 13

Assays of Nucleotide Exchange Using Preloaded GTPases

In assays of nucleotide exchange using preloaded GTPases, G-protein is preloaded with fluorescent nucleotide and the exchange reaction is carried out in a solution containing an excess of non-fluorescent guanine nucleotide. The main use for this assay is for kinetic analysis of guanine nucleotide dissociation rates. Additionally, it can be extended to the study of GEFs, GAPs, GDIs, and effectors.

For example, using Cdc42 preloaded with mant-GDP, the $Cdc42^{(C18A)}$ mutant was shown to function as a dominant negative during the guanine nucleotide exchange reaction. In this experiment, purified wild-type Cdc42 was preloaded with mant-GDP by incubation in a solution containing about 2-fold molar excess mant-GDP, 5 mM EDTA, 10 mM Tris (pH 7.5), 150 mM NaCl, 1 mM DTT, and 5% glycerol (v/v). After 30 minutes at room temperature, $MgCl_2$ was added to a final concentration of 20 mM to terminate nucleotide exchange and Cdc42 was subsequently exchanged into buffer containing 20 mM Tris (pH 7.5), 50 mM NaCl, and 5 mM $MgCl_2$ using gel exclusion chromatography. The protein was then used for a standard guanine nucleotide exchange assay in a solution consisting of 400 nM mant-GDP preloaded Cdc42, 200 nM Dbs (GEF), 20 µM GDP, and 2 µM of either wild type Cdc42 or mutant $Cdc42^{(C18A)}$. The presence of the $Cdc42^{(C18A)}$ mutant slows the ability of Dbs to catalyze release of mant-GDP from wild type Cdc42. This $Cdc42^{(C18A)}$ mutant was subsequently shown to cause a decrease in the G-protein's affinity for guanine nucleotide, resulting in the sequestration of Dbs in a stable complex with $Cdc42^{(C18A)}$ (Rossman et al., *J. Biol. Chem.*, 2002, 277:50893-8).

Example 14

Fluorescence Resonance Energy Transfer (FRET)-Based Assays of Nucleotide Exchange Assays of nucleotide exchange based upon fluorescence resonance energy transfer (FRET) typically rely upon the intrinsic fluorescence emission from tryptophan residues within the GTPase. Tryptophan residues have environmentally sensitive spectroscopic properties resulting in a steady-state fluorescence emission maximum at about 335 nm when excited at 295 nm. Biochemists have taken advantage of this unique spectroscopic property of tryptophan for some time to study structure and folding in a wide variety of proteins (Papp et al., *Photochem. Photobiol.*, 1989, 49:775-84). Traditional approaches typically monitor changes in the fluorescence emission spectra of tryptophan residues resulting from changes in conformation within the protein, i.e., the fluorescence spectrum changes as the microenvironment of the tryptophan residue changes.

However, unlike traditional intrinsic tryptophan fluorescence assays that directly monitor tryptophan fluorescence, typical FRET-based assays rely upon the non-radiative transfer of energy between ultraviolet light-excited tryptophans within the protein under study and nearby fluorophores having overlapping energy spectra (Selvin, *Methods Enzymol.*, 1995, 246:300-34). This energy transfer is extremely sensitive to the distance separating the two fluorophores and has been used to study protein-protein interactions as well as conformational changes in numerous proteins. In a typical nucleotide exchange assay relying on FRET, fluorescence energy from a donor tryptophan can excite an acceptor fluorophore. This energy transfer is observed only when fluorescent nucleotide binds to G-protein and can thereby be used to quantify the amount of nucleotide-bound G-protein. FRET between tryptophan and mant-nucleotide caused by exciting tryptophan ($\lambda_{ex}$=295 nm) results in two useful, reciprocal changes in the fluorescence spectra: (1) emission ($\lambda_{em}$=440 nm) of the mant fluorophore increases while (2) emission ($\lambda_{em}$=335 nm) from tryptophan decreases.

Monitoring increases in mant fluorescence due to energy transfer from excited tryptophan is an alternative approach to directly exciting the mant fluorophore. The benefit of using this approach is an increase in the signal to noise ratio, as exemplified in an experiment showing the spontaneous loading of mant-GTP onto the Ras-related protein Rap2A. The intrinsic nucleotide exchange rate of 100 nM Rap2A was monitored using the fluorescent nucleotide exchange assay with mant-GTP in the absence of a RapGEF. Intrinsic exchange of Rap2A was monitored by either direct excitation of the mant fluorophore at 360 nm, or indirect excitation of tryptophan within the GTPase at 295 nm. Fluorescence emission of the mant fluorophore was then measured at 440 nm. Excitation of tryptophan results in a FRET-based excitation of bound mant-GTP and yields about a 2-fold increase in the signal to noise ratio as compared to excitation of the mant group directly. In this example, fluorescence emission ($\lambda_{em}$=440 nm) of bound mant-GTP via FRET upon excitation of tryptophan ($\lambda_{em}$=295 nm) leads to approximately a 2-fold increase in the signal-to-noise relative to direct excitation of the mant fluorophore ($\lambda_{ex}$=360 nm).

Although FRET-based approaches to studying small GTPase function are extremely sensitive, the requirement for at least one tryptophan residue precludes the study of certain G-proteins, such as Ras, that lack tryptophan. Nevertheless, strategic introduction of a single tryptophan residue using site-directed mutagenesis has been sufficient to allow fluorescence based studies without perturbing the G-protein's activity (Skelly et al., *FEBS Lett.*, 1990, 262:127-30; Antonny et al., *Biochemistry*, 1991, 30:8287-95). Furthermore, FRET-based assays are particularly useful for studying the activation of the Rho subfamily GTPases, due to the presence of a strictly conserved tryptophan residue.

A FRET-based approach can also be used for the biochemical characterization of GEFs responsible for the activation of Rho GTPases (Rossman et al., *EMBO J.*, 2002, 21:1315-26). A single point mutation (Y889F) within the pleckstrin homology (PH) domain of Dbs (Dbl's big sister) is sufficient to abolish the exchange activity of Dbs on both RhoA and Cdc42. Rather than monitoring an increase in mant fluorescence, a decrease in tryptophan fluorescence resulting from FRET is monitored. Tryptophan within RhoA or Cdc42 was excited at 295 nm and steady-state fluorescence was monitored at 335 nm in a buffer initially lacking fluorescent nucleotide and consisting of: 10% glycerol, 50 µg/mL BSA, 20 mM Tris (pH 7.5), 150 mM NaCl, 1 mM DTT, 10 mM $MgCl_2$, 200 nM Dbs (GEF), and 2 µM RhoA or Cdc42 (GTPase). After a period of equilibration, the exchange reaction was initiated by the addition of mant-GTP. RhoA and Cdc42 used for this example were purified in the presence of GDP; therefore, the observed steady-state tryptophan fluorescence in the absence of mant-GTP correlates with 100% GDP-bound. Once the reaction is initiated, Dbs catalyzes loading of mant-GTP until 100% of the GTPase is GTP-bound. Dbs catalyzed loading of mant-GTP onto GTPase causes a decrease in the fluorescence emission of tryptophan due to fluorescence resonance energy transfer between bound mant-GTP and intrinsic tryptophan.

Example 15

Emerging Fluorescence Resonance Energy Transfer (FRET)-Based Techniques for Live Cell Imaging The study of spatial-temporal activation of Ras superfamily GTPases using FRET in living cells is an emerging field in G-protein research. Studies devoted to live cell imaging describe activation and localization of GTPases in response to various stimuli using biosensors that are sensitive to GTPase activation and subsequent interaction with downstream effectors (Hahn et al., *Curr. Opin. Cell Biol.*, 2002, 14:167-72).

Within the cell, Ras GTPases are modified by lipid groups at their C-termini, resulting in localization to the inner membranes of cells. Upon appropriate stimulation, membrane-associated GTPases are activated by GEFs, allowing further downstream interactions with effector proteins generally localized to the plasma membrane. Stimuli, such as a chemoattractant gradient, can induce altered distributions of activated G-protein, resulting in gradients that allow cell polarization. This is especially evident in the case of Rho subfamily GTPases during actin cytoskeletal rearrangement in neutrophils (Gardiner et al., *Curr. Biol.*, 2002, 12:2029-34). Emerging techniques using FRET have allowed investigators to study the highly coordinated events involved in Ras GTPase activation (Macara, *Dev. Cell*, 2002, 2:379-80; Bos, *Nature*, 2001, 411:1006-7).

The use of FRET for real-time live cell imaging of small GTPase activation has been described for Rac (Kraynov et al., *Science*, 2000, 290:333-7; Del Pozo et al., *Nat. Cell Biol.*, 2002, 4:232-9; Tzima et al., *EMBO J.*, 2002, 21:6791-800), Ran (Kalab et al., *Science*, 2002, 295:2452-6; Plafker et al., *J. Biol. Chem.*, 2002, 277:30121-7), Cdc42 (Itoh et al., *Mol. Cell. Biol.*, 2002, 22:6582-6591), as well as Ras and Rap (Mochizuki et al., *Nature*, 2001, 411:1065-8). In each case, activated GTPase is detected by the expression of one or more biosensors. Biosensors typically contain two fluorophores that can interact to yield FRET-based changes in fluorescence emission due to intra- or inter-molecular interactions that vary upon interaction with active GTPases (Hahn et al., *Curr. Opin. Cell Biol.*, 2002, 14:167-72). Alternatively, FRET can be measured between an effector binding domain conjugated to a fluorescent probe and a GTPase fused to green fluorescent protein (GFP) or its variants (Macara, *Dev. Cell,* 2002, 2:379-80; Bos, *Nature,* 2001, 411:1006-7).

For example, activation of Rac fused to GFP was monitored by measuring FRET upon interaction with the Rac-binding domain of p21-activating kinase (Pak1) derivatized with Alexa-546 (Kraynov et al., *Science,* 2000, 290:333-7). This strategy was used to show that platelet derived growth factor (PDGF) stimulation induces moving ruffles of FRET associated with Rac activation and actin polymerization (Kraynov et al., *Science,* 2000, 290:333-7). Similarly, in studies of the nuclear GTPase Ran a biosensor was expressed consisting of the effector binding domain from the yeast Ran-GAP accessory factor Yrb1 separating yellow fluorescent protein (YFP) and cyan fluorescent protein (CFP) (Kalab et al., *Science,* 2002, 295:2452-6). In the absence of GEF, Ran exists in the inactive GDP-bound form and does not interact with the Ran binding domain so that YFP and CFP are in close proximity to facilitate FRET. However, upon co-expression with a RanGEF, such as RCC1, the FRET signal is reduced as binding of Ran to the Ran binding domain disrupts the interaction between the two fluorophores. This approach was used to visualize nuclear Ran activation gradients during interphase (Kalab et al., *Science,* 2002, 295:2452-6).

Example 16

Inhibition of Guanine Nucleotide Dissociation by Effector Coupling

Complexes between activated GTPases and effector proteins are typically stable enough to dramatically decrease the intrinsic guanine exchange cycle of the G-protein. This property of effector proteins has led to the development of assays that correlate guanine nucleotide dissociation rates with binding affinities for GTPase effectors that have been used in the past to determine binding affinity constants between Ras superfamily GTPases and their effectors (Herrmann et al., *J. Biol. Chem.,* 1996, 271:6794-800; Herrmann et al., *J. Biol. Chem.,* 1995, 270:2901-5; Kuhlmann et al., *Biochemistry,* 1997, 36:12027-35).

One example that illustrates inhibition of GTP release upon interaction with effectors shows an interaction of the small GTPase Rap2A with the tandem RBDs of RGS14 (Traver et al., *Biochem. J.,* 2000, 350 Pt 1:19-29; Kimple et al., D. P. *J. Biol. Chem.,* 2001, 276:29275-81). The intrinsic guanine nucleotide exchange rate of Gpp(NH)p-preloaded Rap2A (100 nM) was monitored with mant-GTP in the absence (solid) or presence (dashed) of the RBD tandem repeat (aa 300-447) from the putative Rap2A effector rat RGS14 (1 µM). In this example, 1 mL cuvettes were loaded with 1 µM mant-GTP (in 50 mM Tris pH 7.5, 5 mM $MgCl_2$, 1 mM EDTA at 37° C.) and allowed to equilibrate prior to the addition of 100 nM Rap2A (preloaded with Gpp(NH)p) in the presence or absence of 1 µM of the RGS14 RBD protein. The dissociation of Gpp(NH)p was then measured by excitation of the tryptophan residue. The FRET-mediated excitation of bound mant-GTP was also measured. Binding of the RGS14 RBD repeat region to activated Rap2A prevents the loss of guanine nucleotide from the G-protein, thereby effectively acting as a guanine nucleotide dissociation inhibitor (GDI). Further, the incubation of Rap2A with the RGS14 tandem RBD repeat region slowed the rate of spontaneous nucleotide exchange by about 30% (p<0.05) when compared to that of Rap2A alone. Curves were fit as single exponential functions using GraphPad Prism™ (GraphPad Software, Inc.). Previous studies incorporating this strategy were instrumental in determining binding affinities of Ras with the RBD of Raf and Ra1GDS (Herrmann et al., *J. Biol. Chem.,* 1996, 271:6794-800; Herrmann et al., *J. Biol. Chem.,* 1995, 270:2901-5) and were later applied to biochemical characterization of Ran with its effector RanBP (Kuhlmann et al., *Biochemistry,* 1997, 36:12027-35).

Example 17

Emerging Fluorescence Resonance Energy Transfer (FRET)-Based Assays for Effector Coupling FRET-based assays for effector coupling utilize fluorescent biosensors similar to those used for live cell imaging of G-protein activation. In many cases, the same biosensors expressed in cells can be affinity purified and used for in vitro testing (Kraynov et al., *Science,* 2000, 290:333-7; Kalab et al., *Science,* 2002, 295:2452-6). A FRET-based assay for detecting Rac and Cdc42 interactions with effector proteins has been developed (Graham et al., *Anal. Biochem.,* 2001, 296:208-17). This biosensor consists of the CRIB domain of Pak flanked by an N-terminal green fluorescence protein (GFP) and a C-terminal blue fluorescence protein (BFP); a strategy similar to that described for the study of Ran activation (Kalab et al., *Science,* 2002, 295:2452-6). Activated G-protein binds to the CRIB domain, thereby separating the two fluorophores and reducing the amount of FRET observed. This Cdc42/Rac1 biosensor can be used for in vitro analysis of effector coupling. For example, a putative effector for Cdc42 or Rac could be tested by incubating the candidate protein with the biosensor and GTPase. A true effector would compete with the biosensor for binding of G-protein, thereby increasing the amount of FRET signal from the biosensor.

All publications, patent applications, patents, patent publications and other references cited herein are incorporated by reference in their entireties for the teachings relevant to the sentence and/or paragraph in which the reference is presented.

The foregoing examples are illustrative of the present invention, and are not to be construed as limiting thereof. The invention is described by the following claims, with equivalents of the claims to be included therein.

What is claimed is:

1. A method of identifying a compound having the ability to inhibit guanine nucleotide exchange factor activity, comprising:

a) contacting the compound with a first guanine nucleotide exchange factor and a GTPase and obtaining a baseline fluorescence measurement;

b) contacting the first guanine nucleotide exchange factor and the GTPase without the compound and obtaining a baseline fluorescence measurement;

c) adding a fluorophore-conjugated GTP to the components of (a) and (b), respectively;

d) obtaining fluorescence measurements of the respective components of (c) over time;

e) subtracting the respective baseline fluorescence measurements of (a) and (b) from the fluorescence measurements of (d);

f) comparing the resulting fluorescence values of (e), wherein a decrease in the rate of fluorescence change with the compound as compared with the rate of fluorescence change without the compound identifies a compound potentially having the ability to inhibit guanine nucleotide exchange factor activity;

g) repeating steps a-e with a second guanine nucleotide exchange factor; and h) comparing the resulting fluorescence values of (g), wherein no decrease in the rate of fluorescence change with the compound as compared with the rate of fluorescence change without the compound identifies a compound having the ability to inhibit guanine exchange factor activity.

2. A method of identifying a compound having the ability to inhibit GTPase activity, comprising:
   a) contacting the compound with a guanine nucleotide exchange factor and a first GTPase and obtaining a baseline fluorescence measurement;
   b) contacting the guanine nucleotide exchange factor and the first GTPase without the compound and obtaining a baseline fluorescence measurement;
   c) adding a fluorophore-conjugated GTP to the components of (a) and (b), respectively;
   d) obtaining fluorescence measurements of the respective components of (c) over time;
   e) subtracting the respective baseline fluorescence measurements of (a) and (b) from the fluorescence measurements of (d);
   f) comparing the resulting fluorescence values of (e), wherein a decrease in the rate of fluorescence change with the compound as compared with the rate of fluorescence change without the compound identifies a compound potentially having the ability to inhibit GTPase activity;
   g) repeating steps a-e with a second GTPase; and
   h) comparing the resulting fluorescence values of (g), wherein no decrease in the rate of fluorescence change with the compound as compared with the rate of fluorescence change without the compound identifies a compound having the ability to inhibit GTPase activity.

* * * * *